(12) United States Patent
Nicolaes et al.

(10) Patent No.: US 9,155,756 B2
(45) Date of Patent: Oct. 13, 2015

(54) METHOD FOR THE PREVENTION AND TREATMENT OF SEPSIS

(75) Inventors: Gerardus Anna Franciscus Nicolaes, Sint Geertruid (NL); Christiaan Peter Maria Reutelingsperger, Maastricht (NL); Hendrik Coenraad Hemker, Maastricht (NL)

(73) Assignees: Universiteit Maastricht, Maastricht (NL); Academisch Ziekenhuis Maastricht, Maastricht (NL)

( * ) Notice: Subject to any disclaimer, the term of this patent is extended or adjusted under 35 U.S.C. 154(b) by 0 days.

(21) Appl. No.: 14/131,016

(22) PCT Filed: Jul. 12, 2012

(86) PCT No.: PCT/EP2012/063639
§ 371 (c)(1),
(2), (4) Date: Feb. 19, 2014

(87) PCT Pub. No.: WO2013/007771
PCT Pub. Date: Jan. 17, 2013

(65) Prior Publication Data
US 2014/0162978 A1    Jun. 12, 2014

(30) Foreign Application Priority Data
Jul. 14, 2011 (EP) .................... 11174070

(51) Int. Cl.
*A61K 31/727* (2006.01)
*A61P 31/00* (2006.01)
(52) U.S. Cl.
CPC .................... *A61K 31/727* (2013.01)
(58) Field of Classification Search
CPC .................................................. A61K 31/727
See application file for complete search history.

(56) References Cited

U.S. PATENT DOCUMENTS 5,527,785 A * 6/1996 Bevilacqua et al. ............ 514/56

FOREIGN PATENT DOCUMENTS

| WO | 2006015171 A2 | 2/2006 |
| WO | 2013007771 A1 | 1/2013 |

OTHER PUBLICATIONS

Sepsis, from CDC, pp. 1-2, published on May 22, 2014.*
Sepsis and Septic Shock-Merck Manual, from http://www.merckmanuals.com/professional/critical_care_medicine/sepsis_and_septic_sho . . . , pp. 1-5, accessed Jan. 19, 2015.*
Morrison et al, A Novel Nonanticoagulant Heparin Prevents Vascular Endothelial Cell Dysfunction During Hyperdynamic Sepsis, Shock, 1996, 6, pp. 46-51.*
Cornet et al, The role of heparin and allied compounds in the treatment of sepsis, Thromb Haemost, 2007, 98, pp. 579-586.*
Chandra et al, Sepsis: Emerging Role of Nitric Oxide and Selectins, Clinics, 2006, 6, pp. 71-76.*
Melo, F. R., "Antithrombin-mediated Anticoagulant Activity of Sulfated Polysaccharides: Different Mechanisms for Heparin and Sulfated Galactans," Journal of Biological Chemistry, vol. 279, No. 20, May 14, 2004, pp. 20824-20835.
International Search Report and Written Opinion mailed Aug. 16, 2012 for International Application No. PCT/EP2012/063639, 4 pages.
International Preliminary Report on Patentability dated Jan. 14, 2014 for International Application No. PCT/EP2012/063639, 4 pages.

* cited by examiner

*Primary Examiner* — Julie Ha
*Assistant Examiner* — Li Ni Komatsu
(74) *Attorney, Agent, or Firm* — TraskBritt, P.C.

(57) ABSTRACT

This invention is in the field of medical treatment, in particular the invention provides a method for the prevention and treatment for sepsis or septic shock. The invention provides a novel use of a known medicament, i.e., pentasaccharide-depleted heparin, for use in the treatment or prevention of sepsis, systemic inflammatory response syndrome, severe sepsis or septic shock.

6 Claims, 2 Drawing Sheets

METHOD FOR THE PREVENTION AND TREATMENT OF SEPSIS

CROSS-REFERENCE TO RELATED APPLICATIONS

This application is a national phase application of PCT/EP2012/063639 filed on Jul. 12, 2012, which claims priority to EPO 11174070.0 filed on Jul. 14, 2011.

FIELD OF THE INVENTION

This invention is in the field of medical treatment, in particular the invention provides a method for the prevention and treatment for sepsis or septic shock.

BACKGROUND OF THE INVENTION

Sepsis is a potentially deadly medical condition that is characterized by a whole-body inflammatory state (called a systemic inflammatory response syndrome or SIRS) and the presence of a known or suspected infection. The body may develop this inflammatory response by the immune system to microbes in the blood, urine, lungs, skin, or other tissues. A lay term for sepsis is blood poisoning, more aptly applied to septicemia, below. Severe sepsis is the systemic inflammatory response, plus infection, plus the presence of organ dysfunction.

Septicemia is a related medical term referring to the presence of pathogenic organisms in the bloodstream, leading to sepsis. The term has not been sharply defined. It has been inconsistently used in the past by medical professionals, for example as a synonym of bacteremia, causing some confusion.

Severe sepsis is usually treated in the intensive care unit with intravenous fluids and antibiotics. If fluid replacement is insufficient to maintain blood pressure, specific vasopressor medications can be used. Mechanical ventilation and dialysis may be needed to support the function of the lungs and kidneys, respectively. To guide therapy, a central venous catheter and an arterial catheter may be placed; measurement of other hemodynamic variables (such as cardiac output, or mixed venous oxygen saturation) may also be used. Sepsis patients require preventive measures for deep vein thrombosis, stress ulcers and pressure ulcers, unless other conditions prevent this. Some patients might benefit from tight control of blood sugar levels with insulin (targeting stress hyperglycemia), low-dose corticosteroids or activated drotrecogin alfa (re-combinant protein C).

Systemic Inflammatory Response Syndrome or SIRS is evidence of the body's ongoing inflammatory response. When SIRS is suspected or known to be caused by an infection, this is sepsis. Severe sepsis occurs when sepsis leads to organ dysfunction, such as trouble breathing, coagulation or other blood abnormalities, decreased urine production, or altered mental status.

Sepsis can lead to multiple organ dysfunction syndrome (MODS) (formerly known as multiple organ failure), and death. Organ dysfunction may result from local changes in blood flow, from sepsis-induced hypotension (<90 mmHg or a reduction of ≥40 mmHg from baseline) and from diffuse intravascular coagulation.

Sepsis can be defined as the body's response to an infection. An infection is caused by microorganisms or bacteria invading the body and can be limited to a particular body region or can be widespread in the bloodstream. Sepsis is acquired quickest with infections developed in surgery and physical contact with someone with sepsis.

Bacteremia is the presence of viable bacteria in the bloodstream. Likewise, the terms viremia and fungemia simply refer to viruses and fungi in the bloodstream. These terms say nothing about the consequences this has for the body. For example, bacteria can be introduced into the bloodstream during toothbrushing. This form of bacteremia almost never causes problems in normal individuals. However, bacteremia associated with certain dental procedures can cause bacterial infection of the heart valves (known as endocarditis) in high-risk patients. Conversely, a systemic inflammatory response syndrome can occur in patients without the presence of infection, for example in those with burns, polytrauma, or the initial state in pancreatitis and chemical pneumonitis.

In addition to symptoms related to the provoking infection, sepsis is characterized by presence of acute inflammation present throughout the entire body, and is, therefore, frequently associated with fever and elevated white blood cell count (leukocytosis) or low white blood cell count and lower-than-average temperature, and vomiting. The current concept of sepsis is that the host's immune response to the infection causes most of the symptoms of sepsis, resulting in hemodynamic consequences and damage to organs. This host response has been termed systemic inflammatory response syndrome (SIRS) and is characterized by an elevated heart rate (above 90 beats per minute), high respiratory rate (above 20 breaths per minute or a partial pressure of carbon dioxide in the blood of less than 32), abnormal white blood cell count (above 12,000, lower than 4,000, or greater than 10% band forms) and elevated or lowered body temperature, i.e. under 36° C. (97° F.) or over 38° C. (100° F.). Sepsis is differentiated from SIRS by the presence of a known or suspected pathogen. For example SIRS and a positive blood culture for a pathogen indicates the presence of sepsis. However, in many cases of sepsis no specific pathogen is identified.

This immunological response causes widespread activation of acute-phase proteins, affecting the complement system and the coagulation pathways, which then cause damage to the vasculature as well as to the organs. Various neuroendocrine counter-regulatory systems are then activated as well, often compounding the problem. Even with immediate and aggressive treatment, this may progress to multiple organ dysfunction syndrome and eventually death.

According to the American College of Chest Physicians and the

Society of Critical Care Medicine, there are different levels of sepsis:

Systemic inflammatory response syndrome (SIRS). Defined by the presence of two or more of the following findings:

Body temperature <36° C. (97° F.) or >38° C. (100° F.) (hypothermia or fever).

Heart rate >90 beats per minute.

Respiratory rate >20 breaths per minute or, on blood gas, a $P_aCO_2$ less than 32 mm Hg (4.3 kPa) (tachypnea or hypocapnia due to hyperventilation).

White blood cell count <4,000 cells/mm$^3$ or >12,000 cells/mm$^3$ (<4×10$^9$ or >12×10$^9$ cells/L), or greater than 10% band forms (immature white blood cells). (leukopenia, leukocytosis, or bandemia).

Sepsis. Defined as SIRS in response to a confirmed infectious process. Infection can be suspected or proven (by culture, stain, or polymerase chain reaction (PCR)), or a clinical syndrome pathognomonic for infection. Specific evidence for infection includes WBCs in normally sterile fluid (such as urine or cerebrospinal fluid (CSF));

evidence of a perforated viscus (free air on abdominal x-ray or CT scan; signs of acute peritonitis); abnormal chest x-ray (CXR) consistent with pneumonia (with focal opacification); or petechiae, purpura, or purpura fulminans.

Severe sepsis. Defined as sepsis with organ dysfunction, hypoperfusion, or hypotension.

Septic shock. Defined as sepsis with refractory arterial hypotension or hypoperfusion abnormalities in spite of adequate fluid resuscitation. Signs of systemic hypoperfusion may be either end-organ dysfunction or serum lactate greater than 4 mmol/dL. Other signs include oliguria and altered mental status. Patients are defined as having septic shock if they have sepsis plus hypotension after aggressive fluid resuscitation (typically upwards of 6 liters or 40 ml/kg of crystalloid).

Examples of end-organ dysfunction include the following:

Lungs
  acute lung injury (ALI) ($PaO_2/FiO_2$<300) or acute respiratory distress syndrome (ARDS) ($PaO_2/FiO_2$<200)

Brain
  encephalopathy
    symptoms:
      agitation
      confusion
      coma
    etiologies:
      ischemia
      hemorrhage
      microthrombi
      microabscesses
      multifocal necrotizing leukoencephalopathy Liver
  disruption of protein synthetic function: manifests acutely as progressive coagulopathy due to inability to synthesize clotting factors
  disruption of metabolic functions: manifests as cessation of bilirubin metabolism, resulting in elevated unconjugated serum bilirubin levels (indirect bilirubin)

Kidney
  oliguria and anuria
  electrolyte abnormalities
  volume overload

Heart
  systolic and diastolic heart failure, likely due to cytokines that depress myocyte function
  cellular damage, manifest as a troponin leak (although not necessarily ischemic in nature)
    More specific definitions of end-organ dysfunction exist for SIRS in pediatrics.

Cardiovascular dysfunction (after fluid resuscitation with at least 40 ml/kg of crystalloid)
  hypotension with blood pressure <5th percentile for age or systolic blood pressure <2 standard deviations below normal for age, OR
  vasopressor requirement, OR
  two of the following criteria:
    unexplained metabolic acidosis with base deficit >5 mEq/L
    lactic acidosis: serum lactate 2 times the upper limit of normal
    oliguria (urine output <0.5 ml/kg/hr)
    prolonged capillary refill >5 seconds
    core to peripheral temperature difference >3° C.

Respiratory dysfunction (in the absence of cyanotic heart disease or known chronic lung disease)
  the ratio of the arterial partial-pressure of oxygen to the fraction of oxygen in the gases inspired ($PaO_2/FiO_2$) <300 (the definition of acute lung injury), OR
  arterial partial-pressure of carbon dioxide ($PaCO_2$)>65 torr (20 mmHg) over baseline $PaCO_2$ (evidence of hypercapnic respiratory failure), OR
  supplemental oxygen requirement of greater than $FiO_2$ 0.5 to maintain oxygen saturation ≥92%

Neurologic dysfunction
  Glasgow Coma Score (GCS) ≤11, OR
  altered mental status with drop in GCS of 3 or more points in a patient with developmental delay/mental retardation Hematologic dysfunction
  platelet count <80,000/mm$^3$ or 50% drop from maximum in chronically thrombocytopenic patients, OR
  international normalized ratio (INR) >2
  Disseminated Intravascular Coagulation Renal dysfunction
  serum creatinine ≥2 times the upper limit of normal for age or 2-fold increase in baseline creatinine in patients with chronic kidney disease Hepatic dysfunction (only applicable to infants >1 month)
  total serum bilirubin ≥4 mg/dl, OR
  alanine aminotransferase (ALT) ≥2 times the upper limit of normal In common clinical usage, sepsis specifically refers to the presence of a serious bacterial infection (SBI), such as meningitis, pneumonia, pyelonephritis, or gastroenteritis. in the setting of fever. Criteria with regards to hemodynamic compromise or respiratory failure are not clinically useful in neonates because these symptoms often do not arise in neonates until death is imminent and unpreventable.

The therapy of sepsis rests on antibiotics, surgical drainage of infected fluid collections, fluid replacement and appropriate support for organ dysfunction. This may include hemodialysis in kidney failure, mechanical ventilation in pulmonary dysfunction, transfusion of blood products, and drug and fluid therapy for circulatory failure. Ensuring adequate nutrition—preferably by enteral feeding, but if necessary by parenteral nutrition—is important during prolonged illness.

A problem in the adequate management of septic patients has been the delay in administering therapy after sepsis has been recognized. Published studies have demonstrated that for every hour delay in the administration of appropriate antibiotic therapy there is an associated 7% rise in mortality. A large international collaboration was established to educate people about sepsis and to improve patient outcomes with sepsis, entitled the "Surviving Sepsis Campaign". The Campaign has published an evidence-based review of management strategies for severe sepsis, with the aim to publish a complete set of guidelines in subsequent years.

Early Goal Directed Therapy (EGDT), developed at Henry Ford Hospital by Emaneul Rivers, Md., is a systematic approach to resuscitation that has been validated in the treatment of severe sepsis and septic shock. It is meant to be started in the Emergency Department. The theory is that one should use a step-wise approach, having the patient meet physiologic goals, to optimize cardiac preload, afterload, and contractility, thus optimizing oxygen delivery to the tissues. A recent meta-analysis showed that EGDT provides a benefit on mortality in patients with sepsis. As of December 2008 some controversy around its uses remains and a number of trials are ongoing in an attempt to resolve this.

In EGDT, fluids are administered until the central venous pressure (CVP), as measured by a central venous catheter, reaches 8-12 cm of water (or 10-15 cm of water in mechanically ventilated patients). Rapid administration of several liters of isotonic crystalloid solution is usually required to achieve this. If the mean arterial pressure is less than 65 mmHg or greater than 90 mmHg, vasopressors or vasodilators are given as needed to reach the goal. Once these goals are met, the mixed venous oxygen saturation (SvO2), i.e., the oxygen saturation of venous blood as it returns to the heart as measured at the vena cava, is optimized. If the SvO2 is less than 70%, blood is given to reach a hemoglobin of 10 g/dl and then inotropes are added until the SvO2 is optimized. Elective intubation may be performed to reduce oxygen demand if the SvO2 remains low despite optimization of hemodynamics. Urine output is also monitored, with a minimum goal of 0.5 ml/kg/h. In the original trial, mortality was cut from 46.5% in the control group to 30.5% in the intervention group. The Surviving Sepsis Campaign guidelines recommend EGDT for the initial resuscitation of the septic patient with a level B strength of evidence (single randomized control trial).

Most therapies aimed at the inflammation process itself have failed to improve outcome, however drotrecogin alfa (activated protein C, one of the coagulation factors) has been shown to decrease mortality from about 31% to about 25% in severe sepsis. To qualify for drotrecogin alfa, a patient must have severe sepsis or septic shock with an APACHE II score of 25 or greater and a low risk of bleeding. However, since further trials have failed to replicate this result, the use of activated protein C is controversial and is currently the subject of a large trial that was demanded by the European Medicines Regulator.

During critical illness, a state of adrenal insufficiency and tissue resistance (the word 'relative' resistance should be avoided) to corticosteroids may occur. This has been termed critical illness—related corticosteroid insufficiency. Treatment with corticosteroids might be most beneficial in those with septic shock and early severe acute respiratory distress syndrome (ARDS), whereas its role in other patients such as those with pancreatitis or severe pneumonia is unclear. These recommendations stem from studies showing benefits from low dose hydrocortisone treatment for septic shock patients and methylprednisolone in ARDS patients. However, the exact way of determining corticosteroid insufficiency remains problematic. It should be suspected in those poorly responding to resuscitation with fluids and vasopressors. ACTH stimulation testing is not recommended to confirm the diagnosis. The method of cessation of glucocorticoid drugs is variable, and it is unclear whether they should be weaned or simply stopped abruptly.

In some cases, sepsis may lead to inadequate tissue perfusion and necrosis. As this may affect the extremities, amputation may become necessary.

Prognosis can be estimated with the MEDS score. Approximately 20-35% of patients with severe sepsis and 40-60% of patients with septic shock die within 30 days. Others die within the ensuing 6 months. Late deaths often result from poorly controlled infection, immunosuppression, complications of intensive care, failure of multiple organs, or the patient's underlying disease.

Prognostic stratification systems such as APACHE II indicate that factoring in the patient's age, underlying condition, and various physiologic variables can yield estimates of the risk of dying of severe sepsis. Of the individual covariates, the severity of underlying disease most strongly influences the risk of dying. Septic shock is also a strong predictor of short- and long-term mortality. Case-fatality rates are similar for culture-positive and culture-negative severe sepsis.

Some patients may experience severe long term cognitive decline following an episode of severe sepsis, but the absence of baseline neuropsychological data in most sepsis patients makes the incidence of this difficult to quantify or to study. A preliminary study of nine patients with septic shock showed abnormalities in seven patients by MRI.

In the United States, sepsis is the second-leading cause of death in non-coronary ICU patients, and the tenth-most-common cause of death overall according to data from the Centers for Disease Control and Prevention (the first being heart disease). Sepsis is common and also more dangerous in elderly, immunocompromised, and critically ill patients. It occurs in 1-2% of all hospitalizations and accounts for as much as 25% of intensive-care unit (ICU) bed utilization. It is a major cause of death in intensive-care units worldwide, with mortality rates that range from 20% for sepsis to 40% for severe sepsis to >60% for septic shock.

Septic shock is a medical emergency caused by decreased tissue perfusion and oxygen delivery as a result of severe infection and sepsis, though the microbe may be systemic or localized to a particular site. It can cause multiple organ dysfunction syndrome (formerly known as multiple organ failure) and death. Its most common victims are children, immunocompromised individuals, and the elderly, as their immune systems cannot deal with the infection as effectively as those of healthy adults. Frequently, patients suffering from septic shock are cared for in intensive care units. The mortality rate from septic shock is approximately 25%-50%.

In humans, septic shock has a specific definition requiring several criteria for diagnosis:
  First, SIRS (systemic inflammatory response syndrome) must met by finding at least any two of the following:
  Tachypnea (high respiratory rate) >20 breaths per minute or, on blood gas, a PCO2 less than 32 mmHg signifying hyperventilation.
  White blood cell count either significantly low, <4000 cells/mm$^3$ or elevated >12000 cells/mm$^3$.
  Heart rate >90 beats per minute
  Temperature: Fever >38.0° C. (100.4° F.) or hypothermia <36.0° C. (96.8° F.)
  Second, there must be sepsis and not an alternative form cause of SIRS. Sepsis requires evidence of infection, which may include positive blood culture, signs of pneumonia pneumonia on chest x-ray, or other radiologic or laboratory evidence of infection
  Third, signs of end-organ dysfunction are required such as renal failure, liver dysfunction, changes in mental status, or elevated serum lactate.
  Finally, septic shock is diagnosed if there is refractory hypotension (low blood pressure that does not respond to treatment). This signifies that intravenous fluid administration alone is insufficient to maintain a patient's blood pressure from becoming hypotensive.

A subclass of distributive shock, shock refers specifically to decreased tissue perfusion resulting in ischemia and organ dysfunction. Cytokines released in a large scale inflammatory response results in massive vasodilation, increased capillary permeability, decreased systemic vascular resistance, and hypotension. Hypotension reduces tissue perfusion pressure causing tissue hypoxia. Finally, in an attempt to offset decreased blood pressure, ventricular dilatation and myocardial dysfunction will occur.

When bacteria or viruses enter the blood stream, this produces a condition known as bacteremia or viremia. If the organisms are particularly virulent, or the host is immunocompromised, then the host organism may develop a condition known as systemic inflammatory response syndrome (or SIRS). Sepsis is by definition bacteremia, combined with SIRS. If sepsis worsens to the point of end-organ dysfunction (renal failure, liver dysfunction, altered mental status, or heart damage), then the condition is called severe sepsis. Once severe sepsis worsens to the point where blood pressure can no longer be maintained with intravenous fluids alone, then the criteria have been met for septic shock. The precipitating infections which may lead to septic shock if severe enough include pneumonia, bacteremia, diverticulitis, pyelonephritis, meningitis, pancreatitis, and necrotizing fasciitis.

Most cases of septic shock (approximately 70%) are caused by endotoxin-producing Gram-negative bacilli. Endotoxins are bacterial wall lipopolysaccharides (LPS) consisting of a toxic fatty acid (lipid A) core common to all Gram-negative bacteria, and a complex polysaccharide coat (including O antigen) unique for each species. Analogous molecules in the walls of Gram-positive bacteria and fungi can also elicit septic shock. Free LPS attaches to a circulating LPS-binding protein, and the complex then binds to a specific receptor (CD14) on monocytes, macrophages, and neutrophils. Engagement of CD14 (even at doses as minute as 10 pg/mL) results in intracellular signaling via an associated "Toll-like receptor" protein 4 (TLR-4), resulting in profound activation of mononuclear cells and production of potent effector cytokines such as IL-1 and TNF-α. These cytokines act on endothelial cells and have a variety of effects including reduced synthesis of anticoagulation factors such as tissue factor pathway inhibitor and thrombomodulin. The effects of the cytokines may be amplified by TLR-4 engagement on endothelial cells. TLR-mediated activation helps to trigger the innate immune system to efficiently eradicate invading microbes. At high levels of LPS, the syndrome of septic shock supervenes; the same cytokine and secondary mediators, now at high levels, result in systemic vasodilation (hypotension), diminished myocardial contractility, widespread endothelial injury and activation, causing systemic leukocyte adhesion and diffuse alveolar capillary damage in the lung activation of the coagulation system, culminating in disseminated intravascular coagulation (DIC). The hypoperfusion resulting from the combined effects of widespread vasodilation, myocardial pump failure, and DIC causes multiorgan system failure that affects the liver, kidneys, and central nervous system, among others. Unless the underlying infection (and LPS overload) is rapidly brought under control, the patient usually dies.

PD-1 was found to be up-regulated on monocytes/macrophages during sepsis in human and mice. This up-regulation was related to the up-regulation of IL-10 levels in the blood. Interestingly, Said et al. showed that activated monocytes, which is the case in sepsis, express high levels of PD-1 and that triggering monocytes-expressed PD-1 by its ligand PD-L1 induces IL-10 production which inhibits CD4 T-cell function.

Treatment primarily consists of the following.
1. Oxygen administration and airway support.
2. Volume resuscitation.
3. Early antibiotic administration.
4. Rapid source identification and control.
5. Support of major organ dysfunction.

Among the choices for pressors, a randomized controlled trial concluded that there was no difference between norepinephrine (plus dobutamine as needed for cardiac output) versus epinephrine.

However, dopamine has more beta adrenergic activity, and therefore is more likely to cause arrhythmia or myocardial infarction.

Antimediator agents may be of some limited use in severe clinical situations:

Low dose steroids (hydrocortisone) for 5-7 days led to improved outcomes.

Recombinant activated protein C (drotrecogin alpha) has been shown in large randomized clinical trials to be associated with reduced mortality (Number needed to treat (NNT) of 16) in patients with multi-organ failure. If this is given, heparin should probably be discontinued.

According to the US CDC, septic shock is the 13th leading cause of death in the United States, and the #1 cause of deaths in intensive care units. There has been an increase in the rate of septic shock deaths in recent decades, which is attributed to an increase in invasive medical devices and procedures, increases in immunocompromised patients, and an overall increase in elderly patients. Tertiary care centers (such as hospice care facilities) have 2-4 times the rate of bacteremia than primary care centers, 75% of which are nosocomial infections.

The process of infection by bacteria or fungi can result in systemic signs and symptoms that are variously described. Approximately 70% of septic shock cases were once traceable to Gram staining gram-negative bacilli that produce endotoxins; however, with the emergence of MRSA and the increased use of arterial and venous catheters, Gram-positive cocci are implicated approximately as commonly as bacilli. In rough order of increasing severity, these are bacteremia or fungemic; septicemia; sepsis, severe sepsis or sepsis syndrome; septic shock; refractory septic shock; multiple organ dysfunction syndrome, and death.

35% of septic shock cases derive from urinary tract infections, 15% from the respiratory tract, 15% from skin catheters (such as IVs); over 30% of all cases are idiopathic in origin.

The mortality rate from sepsis is approximately 40% in adults, and 25% in children, and is significantly greater when left untreated for more than 7 days.

Sepsis has a worldwide incidence of more than 20 million cases a year, with mortality due to septic shock reaching up to 70 percent even in industrialized countries.

Despite the manifold of different therapies, there exists a need in the art for reliable, safe, affordable and easily applicable therapies for sepsis and related disorders as presented above.

The present invention addresses the above shortcomings, problems and concerns in that it provides a method for the prevention and/or treatment of sepsis, SIRS, severe sepsis or septic shock.

SUMMARY OF THE INVENTION

The present invention provides a novel use of a known compound in the prevention and treatment of sepsis and similar or related diseases. We have demonstrated that a particular fraction of heparin, i.e. penta-saccharide depleted heparin, is capable of preventing clinical signs of sepsis and related disorders. We have shown that mortality is reduced in mammalians with sepsis or related disorders. Mammalians with sepsis or related disorders also showed a prolonged survival.

DETAILED DESCRIPTION OF THE INVENTION

The present invention provides a pentasaccharide-depleted heparin for use in the treatment or prevention of sepsis, SIRS, severe sepsis or septic shock.

The term pentasaccharide-depleted in this context is used to refer to a fraction of heparin wherein the content of pentasaccharides is substantially reduced in comparison to commercially available heparin.

The term substantially reduced in this context means reduced with at least 10%, such as 20% or 30%, more preferably 40 or 50%, even more preferred, more than 60% or 70% or 80% such as 90% or more than 98% such as more than 99% or even 100%. It is most preferred when the pentasaccharide depleted fraction does not contain any detectable pentasaccharides when tested for thrombin generation as described by Hemker et al., (2003) infra. In the experimental section it is described how a pentasaccharide-depleted heparin may be obtained. It is called LAM therein, abbreviation of Low Affinity Material.

We employed a mouse model for sepsis as previously described (Barton B E, Jackson J V, Infect Immun. 1993 April; 61(4):1496-9). One hour after sepsis was induced, mice received either a control intraperitoneal injection with saline, or with 57 micrograms (10 Units) or 114 micrograms (20 Units) LAM per mouse. The results are illustrated in FIG. 2. Mice treated with a low dose (10 Units) of LAM survived the challenge longer whereas mice treated with 20 Units of LAM all survived the challenge after 96 hours of observation.

EXAMPLES

Example 1

Preparation of Low Affinity Material from Unfractionated Heparin

Unfractionated Heparin (UFH) is a mixture of polysaccharide chains. See Casu, B. (1989). "Structure of heparin and heparin fragments." Ann N Y Acad Sci 556: 1-17 for a review. The composition of the chains and their length varies. Only chains with specific composition have anti coagulant activity. These molecules—so-called pentasaccharide domains—can bind strongly to antithrombin (AT) (Casu, B., P. Oreste, et al. (1981). "The structure of heparin oligosaccharide fragments with high anti-(factor Xa) activity containing the minimal antithrombin III-binding sequence. Chemical and 13C nuclear-magnetic-resonance studies." Biochem J 197(3): 599-609).

When UFH is passed through a column that contains immobilized AT, the molecules that contain the pentasaccharide domain bind to the column, whereas other material passes. Unbound material is called Low Affinity Material (LAM), whereas material that does bind is called High Affinity Material (HAM). LAM is substantially reduced in pentasaccharides and in its anticoagulant activity, whereas HAM has anticoagulant activity.

Example 2

Preparation of an AT-Column

The AT-column was prepared according to the package insert of a 5 ml HiTrap column (GE HEALTHCARE® (provider of laboratory equipment)). After washing the isopropanol from the column ~2.5 mg AT in 5 ml coupling buffer was applied to the column. Then the described procedure to couple the protein and to wash the column was employed (according to the package insert). Finally the column was equilibrated with 140 mM NaCl, 20 mM Tris (pH 7.4).

Example 3

Separation of UFH into LAM and HAM

To the column was applied 2 mg heparin. LAM was eluted with 140 mM NaCl, 20 mM Tris (pH 7.4) and HAM with 2 M NaCl, 20 mM Tris (pH 7.4). The last buffer was applied in a block gradient. In FIG. 1 an example of the elution pattern is shown.

To obtain a large amount of LAM, the procedure described in FIG. 1 was repeated several times.

To determine whether the LAM was free of HAM two tests were used. Firstly, collected HAM was reapplied to the AT-column and run as described in FIG. 1. No HAM-peak was found. Secondly the effect of LAM on thrombin generation was measured. The reaction mixture (120 µl) contained normal pooled plasma in a 1.5× dilution, 3 µl LAM or buffer, 4 µM DOPL (60% DOPC, 20% DOPC and 20% DOPE), 5 pM tissue factor (Innovin), 100 mM $CaCl_2$ and 417 µM ZGGR-AMC. The reaction was started with CaCl2+ZGGR-AMC. Thrombin generation was measured as described by Hemker, H. C., P. Giesen, et al. (2003). "Calibrated automated thrombin generation measurement in clotting plasma." Pathophysiol Haemost Thromb 33(1): 4-15. Thrombin generation was not inhibited by the added 3 µl HAM.

The column fractions containing LAM were collected. The buffer was switched to ammonium bicarbonate (pH 7.8) with Sephadex G-25 medium and the fractions were lyophilized. Dried LAM was weighed and dissolved in phosphate buffered saline to reach the desired concentration.

Example 4

Survival after Experimentally Induced Sepsis in Mice

Male 8 to 12-weeks old C57BL6/J mice were challenged with 360 mg/kg of D-galactosamine (Gal) and 5 microgram/kg *Escherichia coli* lipopolysaccharide (LPS) and studied for 96 hours thereafter. A first series of 13 mice received a saline injection after 1 hour, a second series of 8 mice received 57 micrograms (10 Units) of LAM after 1 hour and a third series of 5 mice received 114 micrograms (20 Units) of LAM after 1 hour.

FIG. 2 shows that mice in the saline control group started to die at 12 hours whereas the first mouse in the 10 Units LAM treated group died after 48 hours. Remarkably, all mice in the 20 U LAM treated group survived after 96 hours.

Figure 1:
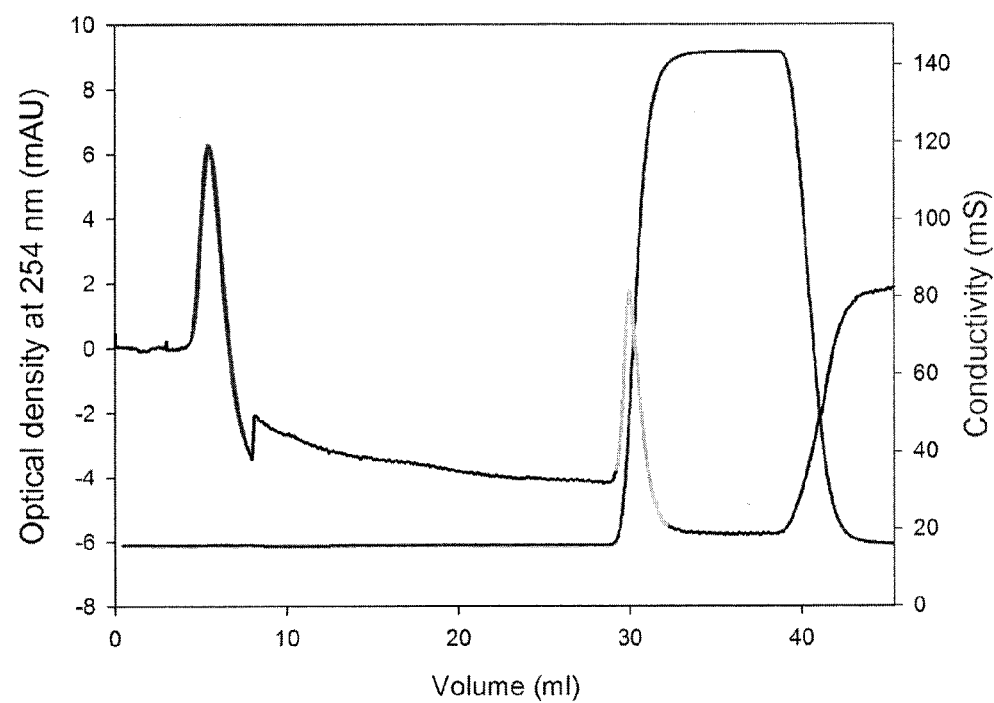
FIG. 1. Separation of UFH into LAM and HAM. 2 mg UFH was applied. The figure shows the optical density at 254 nm, wherein the first peak represents the collected LAM, the second peak contains the collected HAM. The second graph represents the conductivity of the eluted material. LAM was eluted with 1 ml/min and HAM with 4 ml/min.
Figure 2:
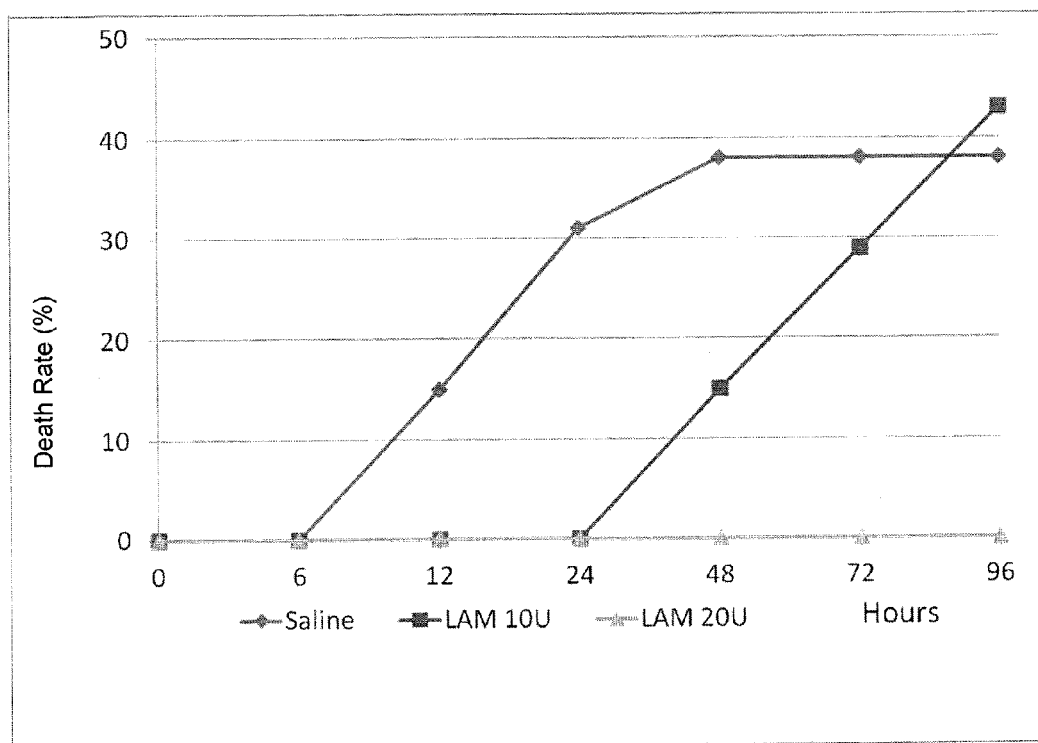
FIG. 2 Death rate (percentage) in experimentally induced sepsis. Experimentally induced sepsis was followed after 1 hour by injection with saline (control, diamonds), 10 Units LAM (squares) and 20 Units LAM (triangles). It is clear that 20 Units LAM protected mice against death from sepsis up to 96 hours after induction.

The invention claimed is:

1. A method for the treatment of a subject suffering from sepsis, systemic inflammatory response syndrome, severe sepsis, or septic shock, the method comprising:
    administering a pentasaccharide-depleted fraction of natural heparin to the subject.
2. The method according to claim 1, wherein the subject is suffering from systemic inflammatory response syndrome.
3. The method according to claim 1, wherein the subject is suffering from severe sepsis.

4. The method according to claim 1, wherein the subject is suffering from septic shock.

5. A method for the treatment of sepsis in a subject, the method comprising:
   administering to the subject a pentasaccharide-depleted fraction of natural heparin.

6. A method for decreasing the rate of mortality of a subject suffering from sepsis, the method comprising:
   administering to the subject a pentasaccharide-depleted fraction of natural heparin.

* * * * *